United States Patent [19]

Bahn et al.

[11] 4,432,905

[45] Feb. 21, 1984

[54] SIMPLIFIED PROCESS FOR THE DEGRADATION OF STEROID-C-22-CARBOXYLIC ACIDS

[75] Inventors: Michael Bahn, Hilden; Wolfgang Preuss, Monheim; Rolf Schmid, Dusseldorf; Rüdiger Wagner, Monheim, all of Fed. Rep. of Germany

[73] Assignee: Henkel Kommanditgesellschaft auf Aktien, Düsseldorf-Holthausen, Fed. Rep. of Germany

[21] Appl. No.: 391,841

[22] Filed: Jun. 24, 1982

Related U.S. Application Data

[63] Continuation-in-part of Ser. No. 262,966, May 12, 1981, abandoned, Ser. No. 262,970, May 12, 1981, abandoned, and Ser. No. 262,971, May 12, 1981, abandoned.

[30] Foreign Application Priority Data

| May 12, 1980 [AT] | Austria | 2534/80 |
| May 12, 1980 [AT] | Austria | 2629/80 |
| Jun. 9, 1980 [AT] | Austria | 3031/80 |

[51] Int. Cl.³ .............................................. C07J 9/00
[52] U.S. Cl. ............................. 260/397.1; 260/397.3; 260/397.4
[58] Field of Search ...................................... 260/397.1

[56] References Cited

U.S. PATENT DOCUMENTS 4,252,732  2/1981  Krbechek et al. ............... 260/397.3
4,255,345  3/1981  Krbechek ........................ 260/397.1

Primary Examiner—Elbert L. Roberts
Attorney, Agent, or Firm—Hammond & Littell, Weissenberger and Muserlian

[57] ABSTRACT

The degradation of steroid-C22-carboxylic acids to the C20-carbonyl steroids is carried out in simplified form and preferably without isolating intermediate reaction products by using 17(20)-steroid-22-carboxylic acids as starting material and directly transforming them into the 20-carbonyl compound through their respective acid halides by the Curtius degradation or by carboxy-inversion degradation. The acetyl substituent thus formed in C17 of the steroid compounds is present in the pharmacologically required configuration.

26 Claims, No Drawings

SIMPLIFIED PROCESS FOR THE DEGRADATION OF STEROID-C-22-CARBOXYLIC ACIDS

This is a continuation-in-part of Ser. Nos. 262,966, 262,970 and 262,971, all filed May 12, 1981, all now abandoned.

BACKGROUND OF THE INVENTION

Steroids containing the $CH_3CO$-residue of progesterone as substituent in the 17-position play a particular role in the field of pharmacologically active steroid compounds and in the synthesis thereof. This acetyl radical in compounds of the progesterone type may be obtained by synthesis starting from 17-one steroids. However, increasing significance is being attributed to synthesis processes in which, starting out in particular from natural steroid compounds of vegetable or animal origin, the originally relatively long-chain substituent in the 17-position is subjected to partial degradation. Thus, European Patent Application as laid open Nos. 004,913 and 0015,305 describe a process for the production of 17C-steroid-α-propionic acid compounds, particularly 3-oxo-pregna-4-ene-20-carboxylic acid ($\Delta^4$-BNC) and/or 3-oxo-pregna-1,4-diene-20-carboxylic acid ($\Delta^{1,4}$-BNC) by microbial side chain degradation on 17C-side chain steroid substrates of natural origin.

BNC-compounds of this type and of related types are still of greater molecular weight by the presence of the carbon atom in the 22-position (present here as a carboxyl group) than steroid compounds of the progesterone type. The utilization of corresponding BNC-compounds for the further synthesis of pharmacologically interesting steroid compound requires degradation of the carboxyl group in C22 or transformation of this substituent present on the C20 into the C20-carbonyl group.

So far as 3-acetoxy-5-ene-BNC is concerned, it is known that the carboxyl group present as a substituent in C20 may be removed by conventional acid degradation using Curtius' method, see Ber. 88 (1955) 883. The product of this degradation is the 20-amino-steroid compound. Its transformation into the 20-keto compound of the progesterone type is relatively complicated.

Many important BNC-compounds containing an additional ene-bond in the 17(20)-position can now be obtained through the degradation of C17-side chain steroid substrates, particularly of natural origin, by microorganisms. Thus U.S. Pat. No. 3,994,933 describes the production of 3-oxo-pregna-4,17(20)-diene-20-carboxylic acid ($\Delta^{4,17}$-BNC), its lower alkyl esters and pharmacologically compatible salts. The acid is obtained by microbial side chain degradation of 17C-steroid compounds.

European Patent Application Nos. 81.1001460.0 and 81.100145.2 and U.S. Pat. No. 4,333,880 describe the production of 20-carboxy-pregna-1,4,17(20)-triene-3-one ($\Delta^{1,4,17}$-BNC) by microbial side chain degradation on 17C-side chain steroid substances. In addition, transformation of the 20-carboxylic acid group into the corresponding ester or the carboxylic acid chloride is described therein.

The copending, commonly-assigned U.S. patent application Ser. No. 262,970, filed May 12, 1981, now abandoned in favor of the present continuation-in-part application, and entitled "New $\Delta^{17(20)}$-BNC-Compounds and a Process For Their Production," priority Austrian Application A-2534/80, filed May 12, 1980, and copending, commonly-assigned U.S. patent application Ser. No. 262,965, filed May 12, 1981, now abandoned in favor of its continuation-in-part Ser. No. 407,790, filed Aug. 13, 1982, entitled "New Pregnane-20-Carboxylic Acid Derivatives and a Process For Their Production," priority Austrian Application A-2535/80, filed May 12, 1980, describe new $\Delta^{4,17(20)}$- and $\Delta^{1,4,17(20)}$-BNC-compounds corresponding to the following general formula:

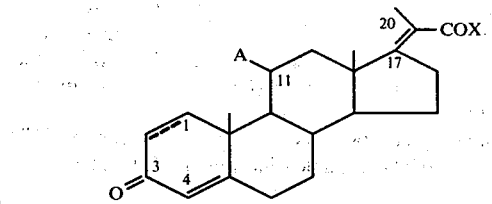

in which A represents α-hydroxyl, β-hydroxyl or, together with the C-atom substituted by A, a carbonyl group and X represents hydroxyl, OK where K is a salt-forming group, OR (where R is a hydrocarbon radical preferably containing no more than 20 carbon atoms and, more particularly, a lower alkyl radical), halogen, particularly chlorine or bromine, or $NH_2$.

These applications also describe the process for introducing the oxygen function into the 11-position.

BNC-compounds, such as those provided with an oxygen function in the 11-position (particularly the 11β-hydroxylated derivatives) may be the starting point for subsequent dehydration to introduce another double bond into the steroid ring skeleton. Under suitable conditions, this double bond is preferably formed in the 9(11)-position, cf, for example, copending, commonly-assigned U.S. patent application Ser. No. 262,971, filed May 12, 1981, now abandoned in favor of the present continuation-in-part, entitled "New Steroid-20-Carboxylic Acid Compounds and a Process For Their Production," priority Austrian Application A-2629/80, filed May 16, 1980.

OBJECTS OF THE INVENTION

The object of the present invention is to provide a process by which transformation of the carboxyl group in C22 present as substituent in the 20-position into the 20-carbonyl group may be carried out more simply. In particular, this process is intended to provide for direct transition from the C-22-steroid carboxylic acid to the C21-steroid compound of the progesterone type without any need for intermediate reaction products to be isolated in between.

The teaching according to the invention is based on the discovery that steroid compounds having the $\Delta^{17(20)}$-structure are particularly suitable for achieving the object according to the invention.

DESCRIPTION OF THE INVENTION

Accordingly, the present invention relates to a simplified process for the degradation of steroid-C22-carboxylic acids into C20-carbonyl steroids which is characterized in that $\Delta^{17(20)}$-steroid-C22-carboxylic acids are subjected to the Curtius degradation or to the carboxy inversion degradation. The corresponding steroid compound of the progesterone type poorer by the carbon atom in the 22-position is preferably directly obtained by this process, i.e., without any need to isolate intermediate reaction products.

Suitable starting materials for the process according to the invention are steroid compounds which contain the propionic acid residue as substituent in the 17-position, this residue being attached in the α-position to an olefinic double bond on C17 of the steroid ring. As will be explained in detail hereinafter, both the Curtius degradation and also the carboxy inversion degradation lead directly to the progesterone structure in C17 where starting compounds of this type are used.

Particularly suitable starting materials for the process according to the invention are $\Delta^{4(5),17(20)}$-BNC compounds which may also contain further olefinic double bonds. Particularly suitable compounds of this type contain additional ene-bonds in the 1(2)-position and/or in the 9(11)-position.

The starting compounds are, therefore, the $\Delta^{17(20)}$-steroid-C22-carboxylic acids having the formulae:

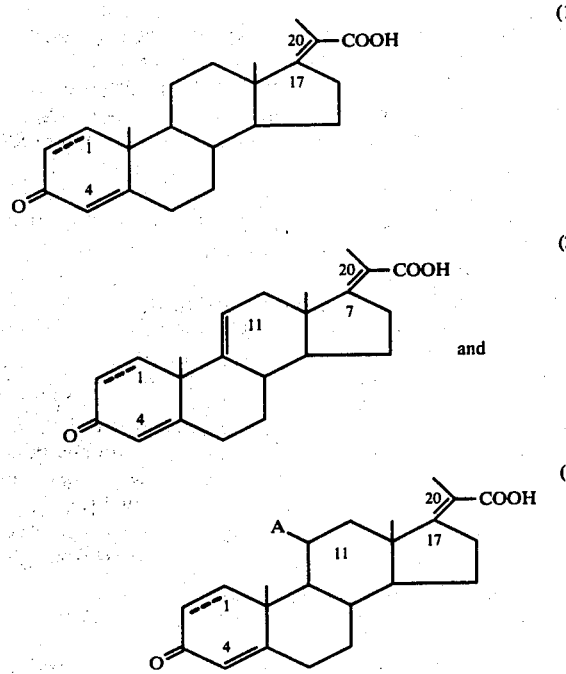

and wherein A represents an α-hydroxyl, a β-hydroxyl or, together with the carbon atom substituted by A, a carbonyl.

Accordingly, the following BNC-compounds are particularly important starting materials for carrying out the teaching according to the invention:

$\Delta^{4,17(20)}$-BNC
$\Delta^{1,4,17(20)}$-BNC
$\Delta^{4,9(11),17(20)}$-BNC
$\Delta^{1,4,9(11),17(20)}$-BNC
11β-hydroxy-$\Delta^{1,4,17(20)}$-BNC, and
11-oxo-$\Delta^{1,4,17(20)}$-BNC.

These starting compounds may be obtained in accordance with the above-mentioned publications and as shown herein.

However, the derivatives of the above-mentioned compounds functionalized with oxygen in the 11-position are also particularly suitable for carrying out the teaching according to the invention. In this case, a hydroxyl group may be present in the 11-position (both the 11α-hydroxyl and, in particular, the 11β-hydroxyl group), although it is also possible for the keto group to be present in the 11-position. The BNC compounds of $\Delta^{4,17(20)}$-BNC and $\Delta^{1,4,17(20)}$-BNC correspondingly functionalized with oxygen are particularly important. Starting compounds of the type in question may also be obtained in accordance with the present application.

According to the invention, degradation of the carboxyl group in C22 leads directly to the 20-carbonyl group both via the Curtius degradation and via the carboxy inversion degradation, the isolation of any intermediate stages formed generally being unnecessary. However, isolation of the acid halide which occurs as an intermediate stage in both methods may be of commercial significance, for example, for obtaining purer products.

The following considerations apply to transformation of the free carboxylic acids into their halides.

The transformation of carboxylic acids into acid halides, particularly acid chlorides, using halogenating agents, such as phosphorus halides, oxalyl halide, or in particular, thionyl halide, is a reaction which has been known per se and widely used for some time, even in the series of 20-carboxy pregnane derivatives.

However, if the reaction conditions described in the literature for the reaction of 3-acetoxy-bis-norcholenic acid with thionyl chloride (see, for example, FIAT Final Report No. 996, pages 24 et seq., and P. L. Julian. E. W. Meyer and H. C. Printy, J. Am. Chem. Soc., 70, 887 (1948) are applied, for example, to $\Delta^{1,4}$-BNC and if the acid chloride thus obtained is subsequently esterified with methanol and the crude product analyzed, the gas chromatogram shows an additional peak, whilst elemental analysis reveals a distinct, initially unexpected Cl-content.

The same applies to an even greater extent where oxalyl chloride is used instead of thionyl chloride.

The reason for the appearance of these unwanted impurities, which considerably reduce the yield of required product and can give rise to purification problems in further reactions with the acid chloride, probably lies in the chlorination accompanied possibly by aromatisation of the A-ring in the steroid skeleton, as known for example for the reaction of androsta-1,4-diene-3,17-dione (ADD) with oxalyl chloride; cf G. W. Moersch et al., J. Org. Chemistry, 29, 2495 (1964).

Surprisingly, the acid halides required in accordance with the invention are formed even under extremely mild reaction conditions under which there is no undesirable co-reaction of other reactive sites of the parent monounsaturated or polyunsaturated BNC-structure. Thus, it has surprisingly been found that for example substantially quantitative acid chloride formation takes place if the following reaction conditions are applied: reaction temperatures below 15° C., preferably below 5° C., and, more particularly, in the range from 0° to 5° C., stoichiometric quantities of the reactants or only a very limited excess of the halogenating agent which preferably amounts to no more than 20 mole percent and, more particularly, to no more than 10 mole percent, and working in the presence of an inert diluent and, if desired, in the presence of small quantities of a basic catalyst.

Examples of inert solvents are halogenated hydrocarbons or—with certain reservations—ethers. Suitable inert solvents are, for example, methylene chloride or chloroform. Suitable halogenating agents are phosphorus halides, particularly PCl₃ or PCl₅, and the corresponding bromides, but above all thionyl halides and particularly thionyl chloride. Catalytic quantities of a base, particularly pyridine or dimethyl formamide, accelerate the reaction, for example in the case of $\Delta^{4,17(20)}$-BNC, but in many cases are unnecessary. It may be desirable to use a catalyst in individual cases.

Depending on other process parameters selected and on the compounds to be reacted with one another, individual process parameters may even lie beyond the limits hitherto quoted. For example, the process temperatures may be in the range from about $-20°$ C. to about 75° C., provided that the formation of unwanted ring halogenation products is avoided at the higher temperatures of this range by suitably controlling the process in other respects. The quantity in which the halogenating agent is used may be considerably in excess of the stoichiometrically necessary quantity, again provided that the other process conditions are suitably adapted. For example, it is possible to use quantities of up to 5 equivalents and preferably up to 3 equivalents of the halogenating agent in special cases. The reaction is normally carried out under normal pressure. The halogenating agent is best added to the solution of the steroid compound to be reacted in the inert solvent. It has been found to be of advantage to use the halogenating agent in the purest possible form. Impurities normally present in the halogenating agent obviously promote unwanted secondary reactions. The halogenating agent is best purified for example with an unsaturated compound, such as linseed oil or, in particular, squalene. These unsaturated components react with the impurities in the halogenating agent and thus reduce the formation of unwanted secondary products to a minimum.

In general, the acid halide may be further processed by one of the methods described in detail in the following either with or without intermediate purification.

Degradation of the carboxyl group in the 22-position may be carried out in accordance with the comprehensive disclosures in the literature in connection with the Curtius degradation of carboxylic acids via their azides to the next lowest primary amines.

The carboxylic acid azides are generally formed in a smooth reaction, cf for example Houben-Weyl "Methoden der organischen Chemie" (1975), Vol. XI/1, pages 862 et seq., particularly page 864.

The modified varient of the Curtius degradation using the two-phase technique, as described in German Offenlegungsschrift No. 22 45 611 for the degradation of fatty acids and dimerised fatty acids, has proved to be particularly effective for the purposes of the invention. The two-phase technique on which this variant is based is characterized in that the acid halide is dissolved in an organic solvent substantially immiscible with water and the reaction of the acyl halide and the metal azide is carried out as a two-phase reaction with an aqueous solution of the azide in the presence of a quaternary ammonium salt as phase transfer catalyst.

This stage of the process according to the invention is preferably carried out under conditions which preclude substantial degradation of the acyl azide formed to the isocyanate. It is preferably carried out at temperatures below about 25° C., more particularly at temperatures below about 15° C. and best at temperatures in the range from about 0° to 15° C. The reactants are preferably moved, for example stirred, during the reaction. However, the mixing effect thus generated should not lead to the formation of a stable emulsion. On completion of the reaction, the organic solution containing the acyl azide may be separated off from the aqueous phase. The organic phase is washed.

Suitable water-immiscible organic solvents are, for example, aliphatic, alicyclic or aromatic hydrocarbons or, in particular, halogenated hydrocarbons, such as methylene chloride or chlorobenzene. The concentration of the acyl halide in the solvent is not critical and may amount for example to between about 5 and 50% by weight. The metal azides used are preferably alkali metal or alkaline-earth metal azides, particularly potassium azide and, above all, sodium azide. The quaternary ammonium salt contains 4 organic radicals of any type, for example alkyl or aryl radicals, on the nitrogen. The total number of carbon atoms is preferably no more than about 30. Corresponding quaternary salts containing up to about 20 carbon atoms in the residues alkylating the nitrogen atom may be particularly suitable. Short-chain alkyl radicals containing from 1 to 5 carbon atoms may be particularly preferred. Radicals of any type may be present as the anion. Halide ions may be particularly appropriate. The quaternary ammonium salt is normally used in only small quantities, for example in quantities of from 0.01 to 10 equivalent percent, based on the halide. The preferred process temperatures are below about 10° C. and, more particularly, in the range from 0° to 5° C.

After the reaction is over, and after the organic phase has been separated off and washed to reduce the content of quaternary ammonium compounds, the steroid-20-carboxylic acid azide formed may be isolated by carefully removing the solvent. In most cases, however, the solution of the acid azide is directly further processed by one of the methods described in the following.

The carboxylic acid azide may be directly converted into the C20-carbonyl compound by a particularly simple reaction. It is known per se that carboxylic acid azides may be directly degraded into the amines containing one less carbon atom by heating with aqueous acids, particularly aqueous acetic acid. However, these amines are not formed in the process according to the invention, instead the required 20-carbonyl compounds are directly formed. The 17(20)-unsaturated amine formed as intermediate is evidently directly rearranged to form the 17(20)-saturated 20-imine which hydrolyses under the reaction conditions to form the 20-keto group. More particularly, the following procedure for example may be adopted:

The solution of the acid azide formed in the water-immiscible solvent is added dropwise to an excess of aqueous acetic acid (concentration for example from 50 to 80% by weight). At the same time, the solvent is carefully distilled off from the reaction mixture. In some cases, it may be advisable to replace the water removed together with the solvent. Finally, the reaction temperature is increased to between 60° and 70° C. After the evolution of gas has abated, the mixture is subjected to steam distillation. The residue is concentrated in vacuo. Water-immiscible solvent and, if desired, aqueous alkali metal hydroxide are added and the mixture is stirred. This is followed by phase separation, after which the organic phase is washed with water and finally evaporated to dryness. The crude 20-carbonyl compound formed may be purified in known manner.

If desired, it is also possible to adopt a multistage procedure in which the acid azide is first converted by the elimination of nitrogen into the isocyanate which may then be subjected to secondary reactions known per se, for example to transformation into the carbonyl compound. In that case, the general principles of the Curtius degradation apply (cf Houben-Weyl, loc. cit., more particularly pages 862 and 865–866). However, the process according to the invention always differs from the normal course of the Curtius degradation in the formation of the 20-carbonyl group instead of a 20-amino group.

It has surprisingly been found that the steric configuration of the substituent thus formed in C17 corresponds to the pharmacologically required configuration. This was not foreseeable either.

In the other variant of the process according to the invention, the carboxyl group is degraded by the carboxy inversion reaction. In this case, the acid halide is reacted with a peracid, followed by hydrolysis of the rearrangement product formed from the mixed anhydride. This carboxy inversion reaction is described in detail in J. Org. Chemistry 30, 3760 (1965)—D. B. Denney, N. Sherman "Degradation of Acids to Alcohols by the Carboxy-Inversion Reaction". Surprisingly, this degradation process may also be successfully applied to steroid carboxylic acids and their corresponding halides although the steroid skeleton of these carboxylic acids contains functional groups in several places. The fact that the process known per se could be so smoothly applied had not been expected. In the case of the 17(20)-steroid compounds used in accordance with the invention, the 20-carbonyl derivatives of the progesterone type are again simultaneously formed as direct products of the process. In this case, too, the configuration formed in the 17-position corresponds to the pharmacologically required configuration. This was not foreseeable either.

According to the invention, m-chloroperbenzoic acid is preferably used as the peracid for forming the mixed acid anhydride. This compound is available in commercial quantities, is relatively safe to handle and ensures a smooth reaction. However, other peracids may be used instead of m-chloroper-benzoic acid. In that case, it is preferred to use aromatic peracids, particularly those containing an electron-attracting residue on the aromatic nucleus, such as p-nitroperbenzoic acid.

The reaction of the steroid carboxylic acid chloride with the peracid, particularly with m-chloroperbenzoic acid, is carried out at temperatures in the range from −50° C. to room temperature. The preferred reaction temperatures are in the range from −10° to −30° C.

The reaction is best carried out in an inert solvent in the presence of a base. The solvents used are, for example, halogenated hydrocarbons, such as methylene chloride or chloroform, ethers such as diethyl ether or tetrahydrofuran, nitriles, such as acetonitrile, acid amides, such as dimethyl formamide, or ketones, such as acetone for example. The preferred inert diluents are solvents having a certain polarity. Particularly suitable bases are tertiary nitrogen bases such as, for example, pyridine, methyl pyridines, N,N-dimethylamino pyridine, triethylamine or ethyl diisopropylamine. It is possible to use both cyclic and also open-chain tertiary amines. However, inorganic bases components particularly basic salts of strong bases and weak, particularly volatile, acids may also be used. A suitable example is lithium carbonate. The base is preferably used in such quantities that the hydrogen halide formed during the reaction can be bound.

The reaction is preferably carried out by adding the peracid to the solution of the steroid-carboxylic acid halide in the inert solvent after cooling to the required initial reaction temperature, for example after cooling to −30° C., and then carefully adding the basic component in portions with stirring and cooling. The reaction mixture is then left for a prolonged period, for example overnight, to heat to room temperature, after which most of the solvent is distilled off. The intermediate product formed may be isolated, although it is preferably directly further processed.

In the following reaction step, the reaction product initially formed is subjected to hydrolysis. Hydrolysis is preferably carried out under basic conditions, best under basic/alcoholic conditions. Alcoholic potassium or sodium hydroxide for example may be used for hydrolysis. Hydrolysis is preferably carried out at moderate temperatures, for example at temperatures of the order of 0° C. The basic component is preferably used in an excess amounting to several times the quantities of acid used. For example, the quantity of base used for hydrolysis may amount to between 3 and 8 times the stoichiometric quantity, based on the steroid carboxylic acid. In this case, the base is preferably used in quantities of from 4 to 6 times the stoichiometric quantity.

On completion of the reaction, the hydrolysis product is concentrated and then taken up in an inert water-immiscible solvent, for example methylene chloride, washed and concentrated to dryness.

In this case, too, the 20-carbonyl compound of the progesterone type is directly obtained as the reaction product. The 17(20)-unsaturated 20-hydroxyl compound formed as intermediate is rearranged to form the 20-keto compound.

During their production, the starting materials according to the invention frequently accumulate together with more or less large quantities of corresponding, but 17(20)-saturated BNC compounds. According to the invention, it is possible to separate the 17(20)-unsaturated BNC-compounds before they are reacted from the corresponding saturated components, although mixtures of the 17(20)-unsaturated and saturated BNC-compounds may also be subjected to one of the described degradation reactions and the reaction product thus obtained separated up to recover the 20-carbonyl compounds.

U.S. Pat. No. 3,994,933 describes the production of 3-oxo-pregna-4,17(20)-diene-20-carboxylic acid ($\Delta^{4,17}$-BNC), its lower alkyl esters and pharmacologically compatible salts. In this case, too, the acid is obtained by the microbial side chain degradation of 17C-steroid compounds.

U.S. Pat. No. 4,333,880 describes the production of 3-oxo-pregna-1,4,17(20)-triene-20-carboxylic acid ($\Delta^{1,4,17}$-BNC).

The new steroid-20-carboxylic acid derivatives, useful as starting materials, according to the invention are also derived from two basic types, namely the steroid-20-carboxylic acids—each containing the oxygen function Y in the 11-position—corresponding to $\Delta^{1,4,17}$-BNC and to $\Delta^{4,17}$-BNC, which are new compounds.

By virtue of the additional double bond in the 17(20)-position, these new compounds according to the invention are particularly suitable for use as intermediate products for the production of pharmacologically active steroid compounds. The multiple reactive centres of these compounds, particularly in conjunction with the double bond in the 17(20)-position, facilitate their transformation into known pharmacologically active components of the steroid group.

In another embodiment, the present invention relates to the process for producing new $\Delta^{4,17(20)}$-and/or $\Delta^{1,4,17(20)}$-BNC-compounds corresponding to general formula 3 below.

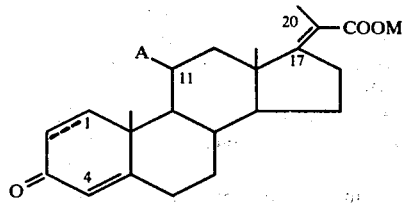

(3)

In formula 3 above, A is a hydroxyl group (both an α-hydroxyl group and also a β-hydroxyl group) or forms a carbonyl group together with the C-atom substituted by A in the 11-position of the steroid ring skeleton. M may have various meanings. In particular, M represents hydrogen. In this case, the compounds corresponding to general formula 3 above are the free carboxylic acids. In addition, M may represent a salt-forming group, i.e. a cation. The cations in question may be both metal cations, particularly alkali metal and/or alkaline-earth metal cations, and also ammonium or organic cations. M may also represent a hydrocarbon radical which preferably contains no more than 20 carbon atoms and, in particular, no more than 10 carbon atoms. Particular significance is attributed to simple alkyl radicals, for example $C_1$ to $C_5$, and especially to the methyl radical.

In another embodiment, the present invention relates to the process for producing new $\Delta^{4,17(20)}$-and/or $\Delta^{1,4,17(20)}$-BNC-compounds corresponding to general formula 3 below

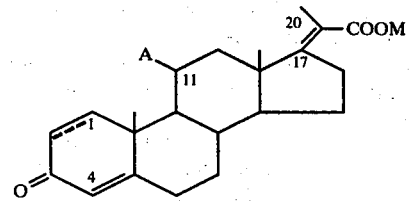

(3)

in which A represents hydroxyl or, together with the C-atom substituted by A, a carbonyl group and M represents hydrogen, a preferably lower alkyl radical, particularly the methyl radical, or a salt-forming group. The process according to the invention is characterized in that the structurally similar BNC-compounds, but without any oxygen in the 11-position, are hydroxylated in the 11-position in known manner under aerobic conditions in an aqueous nutrient medium using microorganisms capable of 11-hydroxylation and if desired, the product obtained is chemically transformed into the end products corresponding to general formula 3 above.

The starting materials for the process according to present invention have the following structure:

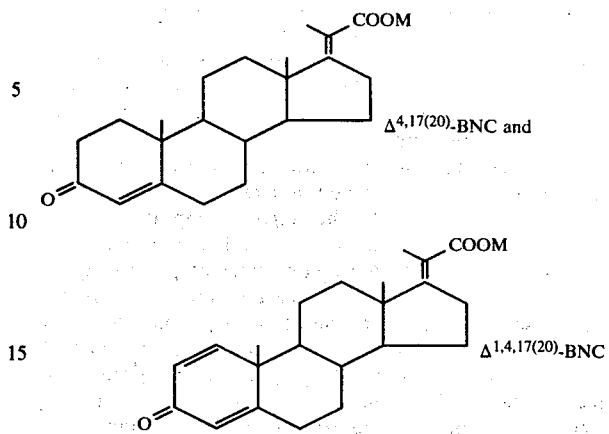

Preparation of these compounds is given in U.S. Pat. No. 3,994,933 and No. 4,333,880.

According to the invention, these starting compounds are modified by microbial oxidation into compounds corresponding to general formula 3.

High pharmacological activity generally requires the 11-β-hydroxyl or 11-oxo configuration. Steroids β-hydroxylated in the 11-position are obtained either by using microorganism strains which introduce a hydroxyl group such as this stereoselectively or by using other microorganisms which hydroxylated substantially or completely stereoselectively in the 11-β-position. In this case, the 11-β-hydroxylated steroids are obtained by chemical oxidation to the 11-ketone in a first step, followed by reduction with a suitable reducing agent. The 11-β-hydroxyl compound can be stereoselectively formed. So far as the relevant literature on this subsequent chemical transformation is concerned, reference is made for example to L. F. Fieser, M. Fieser "Steriode (Steroids)" Verlag Chemie (Weinheim 1961), pages 737 et seq, and to the original literature reference cited therein, J. Am. Chem. Soc. 77, 4436 (1955).

The BNC starting compounds used in accordance with the invention containing the additional olefinic double bond in the 17(20)-position may also be oxidized largely selectively in the 11-position. The particular structure of the oxidation products is determined by the microorganisms selected. Accordingly, it is possible to obtain 11-α-hydroxyl compounds, 11-β-hydroxyl compounds or mixtures of these compounds. The 11-oxo compounds may also be the direct oxidation product, although they may also be produced in a separate process step by chemical oxidation from previously obtained 11-α-and/or -β-hydroxyl compounds.

Oxidation in the 11-position using microorganisms, particularly from the class of fungi, may be carried out under culture conditions known from the literature. In this connection, reference is made to Rehm's book entitled "Industrielle Mikrobiologie (Industrial Microbiology)" Springer (1967), pages 518 to 538 and to the original literature reported therein.

Transformation of the starting compounds substituted in the 11-position is carried out by culturing for example the microorganisms known from the literature which are suitable for this transformation under aerobic conditions in an aqueous nutrient medium of standard composition in the presence of the BNC-starting compounds to be transformed.

The BNC-starting compounds used may be both the corresponding free acids (or their salts soluble or partly soluble in the aqueous nutrient solution) and also directly an ester, particularly the methyl ester of the free acid. However, it is preferred to use the free acid or a salt thereof which is at least partly soluble in the aqueous nutrient medium.

The microbial transformation process is carried out in known manner, as described in detail in the cited literature. Thus, for example, the steroid compound chosen as the starting material may be added to the culture during the incubation period or, alternatively, it may be introduced into the nutrient medium before inoculation of the selected microorganisms. It is possible to use a steroid compound or even a mixture of several steroid compounds. The steroid compounds are preferably used in the culture in quantities of from about 0.1 to 100 g/l. The optimal concentration of the starting compound to be transformed in the culture step is generally dependent upon the strain and may be determined in each case by simple preliminary tests. In general, the concentration of the steroid starting compound in the medium is preferably no more than 50 g/l and, in many cases, no more than 25 g/l, although it may be advantageous to use quantities of more than 1 g/l.

It may also be of advantage not to add the substrate to be subjected to the oxidation reaction to the reaction medium all at once, but instead to make the addition gradually as the reaction progresses. In this embodiment, the starting substrate is preferably added substantially continuously to the reaction mixture during the oxidative transformation process. In many cases, the yield of the required products may be increased in this way.

The culture is grown in a nutrient medium which contains a conventional metabolisable carbon source and the nutrient and growth materials normally required by these microorganisms. Materials particularly favorable to the growth of the microorganisms are, for example, glucose, fructose, sucrose, glycerol, starch, dextrin and sugar-containing waste materials. Suitable nitrogen sources are ammonium salts, nitrates, peptone, corn spring water, soya flour, vinasse and fishmeal. Fermentation accelerators, such as yeast extract and vitamins may also be added. In addition, the nutrient medium best contains inorganic salts, such as sodium, potassium or ammonium phosphates.

Emulsification of the starting material in the nutrient medium is preferably carried out using known emulsifiers, for example fatty acid sorbitan esters, or their ethylene oxide adducts, polyoxyethylene monolauryl ether or fatty acid ethanol amides.

The culture medium used is best sterilized by heating before the beginning of the bacterial culture step. After it has been cooled and inoculated with a suitable preliminary culture of the transforming microorganism strain, the culture medium is incubated at 25° to 55° C. and preferably at 27° to 30° C. The pH-value of the nutrient solution is in the range from pH 4 to pH 8.5. The culture is supplied with oxygen by shaking, stirring or the introduction of gas and is incubated until the oxidation reaction has progressed to the required extent. The oxidation reaction generally takes from 24 to 160 hours, depending on the substrate, the concentration and the other fermentation conditions.

The oxidation product obtained in this way, which is normally enriched in the fermentation broth, may be recovered from the reaction mixture in known manner. Thus, the oxidized BNC-compounds may be isolated from the reaction product by extraction with organic solvents, if desired using exchanger columns. Details of this may be found for example in European Patent Application No. 004913 published on the 31.10.1979—in that case with reference to isolation of the BNC-compounds formed.

Isolation of the hydroxylated BNC-compounds from the fermenter liquid may also be carried out particularly easily in accordance with the present invention by precipitation in the acid range.

The isolated BNC-compounds having an oxygen function in the 11-position may be purified by recrystallization.

Particularly important compounds corresponding to general formula 3 are the 11-$\beta$-hydroxy-$\Delta^{1,4,17(20)}$-BNC, its salts and esters. Another particularly important compound according to the invention is 11-oxo-$\Delta^{1,4,17(20)}$-BNC and the corresponding derivatives of this acid as mentioned above.

Microorganisms cultures suitable for carrying out the process according to the invention are, for example, the fungus cultures capable of 11-$\beta$-hydroxylation of the Curvularia and Cunninghamella strains and the fungus cultures capble of 11-$\alpha$-hydroxylation of the Aspergillus, Sclerotium, Glomerella, Trichothecium, Absidia or Rhizopus strains, such as for example *Curvularia lunata* (NRRL 2380), *Cunninghamella blakesleana* (ATCC 8688b), *Cunninghamella bertholletiae* (NRRL 1378), *Cunninghamella verticillata* (ATCC 8983), *Cunninghamella elegans* (ATCC 9245), *Aspergillus ochraceus* (NRRL 405), *Aspergillus niger* (NRRL 3228), *Sclerotium hydrophilum* (IFO 5293), *Glomerella cingulata* (ATCC 10 534), *Trichothecium roseum* (ATCC 8685), *Absidia orchidis* (ATCC 6811) and *Rhizopus stolonifer* (ATCC 6227b).

Submerse cultures are grown in a suitable, aerated nutrient medium under the culture conditions normally used for microorganisms of this type. The substrate is then added to the cultures in the manner explained earlier on and fermentation continued until maximal substrate transformation is reached.

Suitable substrate solvents are, for example, methanol, ethanol, glycol monomethyl ether, dimethyl formamide or dimethyl sulfoxide.

The optimal substrate concentration, substrate addition time and fermentation period depend upon the structure of the substrate used and upon the type of microorganisms used. As is generally necessary in microbiological steroid transformations, these values have to be determined in each individual case by preliminary tests that are well known to the expert.

European Patent Application No. 11235, which is not a prior publication, describes 9-hydroxylated BNC-compounds and a process for their production. The description relates in particular to 9$\alpha$-hydroxy-pregna-4,17(20)-diene-3-one-20-carboxylic acid.

9$\alpha$-OH-$\Delta^4$-BNC is described in U.S. Pat. No. 4,062,880 which also mentions the transformation of its methyl ester into the ester of $\Delta^{4,9(11)}$-BNC by dehydration.

In a further embodiment, therefore, the present invention relates to new $\Delta^{4,9(11),17(20)}$-pregna-3-one-20-carboxylic acid compounds and related compounds having the formula 2 above.

Accordingly, the invention also provides new BNC compounds which are olefinically unsaturated at least 3 times, which have the 4-ene-3-one or 1,4-diene-3-one structure in the A-ring of the steroid system, which contain in the 20-position a carboxyl group or, as functional derivatives, an ester group, a carboxylic acid halide group or a carboxylic acid amide group, which additionally contain an olefinic double bond in the 9(11)-position and which contain another olefinic double bond in the 17(20)-position.

If an ester residue is present in the 20-position, the esterifying alcohol preferably contains no more than 20 carbon atoms. The alcohols in question may be any aliphatic, alicyclic or aromatic alcohols. Alcohols containing no more than 10 carbon atoms are preferred. Particular significance is attributed to the lower alcohols containing from 1 to 5 carbon atoms. Residues of straight-chain or branched alkanols may have particular significance.

It has also been found in accordance with the present invention (and this is another subject of the present invention) that the new 9(11)-unsaturated compounds may readily be obtained from the structurally similar preliminary stages which are saturated in the 9(11)-position and carry a hydroxyl group either in the 11-position or in the 9-position. The hydroxyl group in the 9-position is present in the α-position, whereas in the 11-position the 11β-position may be preferred. If starting compounds of this type are subjected to dehydration, water may be split off in the 9(11)-position and the olefinic bond required in accordance with the invention simultaneous formed in that position.

The starting compounds for the process according to the invention are described in the cited prior art and above. Their dehydration to form the compounds of formula I according to the invention is preferably carried out using dehydrating agents at normal or only moderately elevated temperatures. Temperatures of up to at most around 80° C. are particularly preferred. In particular, it may be desirable not to exceed temperatures of the order of 50° C. It can be of particular advantage to work at temperatures in the range from −10° to +25° C.

Any known chemical dehydrating agents for eliminating water from secondary or tertiary alcohols are suitable for carrying out the process according to the invention providing they do not enter into undesirable secondary reactions with the starting material. Acid dehydrating agents, particularly corresponding mineral acids, for example sulfuric acid, phosphoric acid or hydrochloric acid, or mineral acid derivatives may be used with advantage. It is also possible to apply a treatment with N-halogen amides or N-halogenimides and $SO_2$, as described in British Pat. No. 869,815. The compounds to be dehydrated may be dissolved in inert solvents, for example hydrocarbon compounds.

One particularly important aspect of the invention concerns compounds corresponding to general formula 2, where the —COOH is replaced by —COX and X is halogen, particularly chlorine, and their production. These acid halides are for example important intermediate products for subsequent chemical reactions involving transformation of the substituent in the 17-position of the steroid skeleton. The 9(11)-ene-20-carboxylic acid halides which are required in accordance with the invention may surprisingly be formed under extremely mild reaction conditions under which there is no undesirable co-reaction of other reactive sites of the parent polyunsaturated BNC-structure.

The carboxylic acid halide formed may either be readily hydrolyzed to form the free acid, reacted with alcohols of the type mentioned to form the corresponding esters or converted with ammonia or an ammonia-yielding compound into the carboxylic acid amide. The various new compounds according to the invention may be conveniently obtained in this way.

As already mentioned, the 9(11)-ene-20-carboxylic acid halides requires in accordance with the invention are surprisingly formed under such mild reaction conditions that there is no undesirable co-reaction of other reactive sites of the parent polyunsaturated BNC structure. Thus, it has been found that for example substantially quantitiative dehydration accompanied by acid chloride formation takes place when the following reaction conditions are applied reaction temperatures below 15° C., working in the presence of an inert diluent and in the presence of a basic compound. Suitable inert solvents are, for example halogenated hydrocarbons or—with certain reservations—ethers. Suitable inert solvents are, for example, methylene chloride or chloroform. The basic compounds used may be above all a tertiary N-base, particularly pyridine or dimethyl formamide, best employed in quantities of at least 2 moles and preferably at least 3 moles per mole of steroid carboxylic acid.

In the embodiment which has just been described (simultaneous dehydration and formation of the carboxylic acid halide group), the halogenating agent is used in an excess over and above the quantity required for forming the carboxylic acid halide group. In general, the halogenating agent is used at least in an approximately 1-molar excess. In addition, it is of advantage to avoid too large an excess. The excess in which the halogenating agent is used is preferably in the 1- to 3-molar range and preferably in the 1- to 1.5-molar range. Suitable halogenating agents are phosphorus halides, particularly $PCl_3$ or $PCl_5$, and the corresponding bromides, but above all thionyl halide and, in particular, thionyl chloride. The halogenating agent is best added to the solution of the steroid compounds to be reacted in the inert solvent. It has been found to be of advantage to use the halogenating agent in the purest possible form. Any impurities present in the halogenating agent obviously promote undesirable secondary reactions. The halogenating agent is best purified for example with an unsaturated compound, such as linseed oil or, in particular, squalene. These unsaturated components react with the impurities in the halogenating agent and thus reduce the formation of undesirable secondary products to a minimum.

The new carboxylic acid amides according to the invention may be obtained from the acid halides by reacting the 20-carboxylic acid halide with ammonia or with an ammonia-yielding compound. This reaction is best carried out at temperatures in the range from about −20° C. to about 80° C. and preferably at temperature in the range from about −5° C. to about 35° C. The ammonia or the compound which yields ammonia under the reaction conditions is used in at least substantially equimolar quantities. Suitable quantities in which to use the ammonia or the ammonia-yielding compound are for example from 1.1 to 5 equivalents (based on acid halide) and preferably from about 1.2 to about 3 equivalents. If an ammonia-yielding compound is used rather than ammonia itself, ammonium hydroxide is particularly suitable for this purpose.

Reaction of the 20-carboxylic acid halide with ammonia or the ammonia-yielding compound is again preferably carried out in an organic solvent, for example in halogenated hydrocarbons, as mentioned above. In this case, too, a particularly suitable inert solvent is methylene chloride or chloroform.

If ammonium hydroxide is used as the ammonia-yielding compound, an aqueous phase accumulates in addition to the organic phase in the reaction mixture. The reaction product may be recovered by simple phase separation or even by separating off the amide precipitated in solid form.

The organic phase separated off is best repeatedly washed with water, subsequently dried, for example with calcium sulfate and filtered. The organic solvent used as the inert diluent is separated off, after which the carboxamido compound may be further purified in known manner.

Any hydrohalic acid which is given off during the reaction between the carboxylic acid halide and the ammonia may be bound by an excess of ammonia or ammonium hydroxide, although a basic component may also be used for binding the acid liberated.

EXAMPLES

The following examples are illustrative of the practice of the invention.

EXAMPLE 1

11-$\beta$-hydroxy-$\Delta^{1,4,17}$-BNC

The strain *Cunninghamella blakesleana* ATCC 8688a was aerobically cultured in a 2 liter Erlenmeyer flask containing 600 ml of nutrient solution having the following composition:

0.15% by weight of $KH_2PO_4$
0.20% by weight of $NaNO_3$
0.30% by weight of peptone
0.50% by weight of yeast extract
3.00% by weight of glucose
pH 5.8

The culture was grown for 48 hours at 30° C. in a shaking machine (shaking frequency 140 r.p.m.), after which 0.1% by weight of "Tween 80" (polyoxyethylene sorbitan monooleate) and 0.2% by weight of $\Delta^{1,4}$-BNC containing 20% of $\Delta^{1,4,17}$-BNC were added and the culture incubated for another 72 hours. The transformation products obtained included (percent of the $\Delta^{1,4,17}$-BNC used): 55% of 11-$\beta$-hydroxy-$\Delta^{1,4,17}$-BNC In this and the following Examples, the pure products were obtained as follows:

After termination of the biotransformation process, the cells were separated off by centrifuging (5 mins. at 10,000 g) and the centrifuged product (1 l) was extracted with 2×1 l of dichloromethane in a separation funnel. The cell mass separated off was also extracted with methylene chlorine or THF. The combined organic extracts were evaporated in vacuo to dryness in a rotary evaporator.

The syrupy residue (2 g) was dissolved in 150 ml of a mixture of methanol/dichloromethane (7:3) and purified as follows over 25 ml of an anion exchanger (Dowex 1×2):

1. Removal of undesirable constituents, for example emulsifiers, of the medium by percolation using another 4×25 ml of a solvent mixture of methanol and dichloromethane (7:3).

The purified percolates are discarded.

2. Elution of the hydroxylated BNC-derivatives with 250 ml of a mixture of 12.3 g of concentrated HCl, 30 ml of dichloromethane, 4.8 g of water, made up with methane to 250 ml.

The eluate was concentrated to 50 ml and the hydroxylated BNC derivatives were precipitated by the addition of 150 ml of distilled water.

The aqueous solution was extracted with 2×100 ml of dichloromethane and the combined organic extracts were dried in vacuo in a rotary evaporator.

For further working up, the methyl esters of the hydroxylated BNC-derivatives were prepared by reacting 2 g of the residue with N=[(tolylsulfonyl-(4)]-N-methyl nitrosamide in accordance with Instruction Pamphlet No. 7/230/4.5/266 of the Merck Company of Darmstadt.

Following removal of the solvent, the residue was taken up in dichloromethane (20 mg/ml) and subjected to preparative liquid chromatography under the following conditions:

(a) Column: Dupont column, Part No. 899000001, filling silica gel, mean particle size 7$\mu$, column length 250 mm, external diameter 25.4 mm.

(b) Eluent: isoctane/isopropanol (95:5)

(c) Conditions: throughflow 50 ml/min., 70 bar, approx. 313 K (d) Detection: UV-detector, 254 nanometers.

The fraction thus separated up was then characterized by various analytical methods as described in the following.

EXAMPLE 2

11-oxo-$\Delta^{1,4,17}$-BNC 10 mg of 11-$\beta$-hydroxy-$\Delta^{1,4,17}$-BNC are dissolved in 1 ml of absolute $CH_2Cl_2$ and the resulting solution is quickly added to a suspension of 10 mg of pyridinium chlorochromate in 1 ml of absolute $CH_2Cl_2$. The suspension is stirred for 1 hour at room temperature and then filtered over a short silica gel column (eluent: $CH_2Cl_3/CH_3OH$ 4:1). Concentration of the eluate leaves 8 mg of a crystalline residue which is pure according to analysis by thin layer chromatography.

The methyl ester was prepared from this compound in accordance with Example 1.

The elementary composition and structural data of the two compounds are shown in Table 1.

TABLE 1

| | Characterisation of the Products | | | | | | | | |
|---|---|---|---|---|---|---|---|---|---|
| | Elementary composition | | $^1$H—NMR-spectrum[1] | | | IR-spectrum[2] | | Mass spectrum[3] | | |
| | % C | % H | Chemical displacement assignment | | Multiplicity | Ester group | keto group C11 | OH | M$^+$ | m/e[4] |
| 11-$\beta$-hydroxy-$\Delta$1,4,17-BNC-methyl ester | calc: 74.56 obs: 74.6/74.6 | 8.16 8.36/8.38 | 1.21 1.46 1.94 3.68 4.43 6.02 6.19/6.21 | 18-$CH_3$ 19-$CH_3$ 21-$CH_3$ 0-$CH_3$ 11-CH  ABC-system | s s t (J = 2.0H$_z$) s m | 1720 | — | 3560 | 370 | 121.293 |

TABLE 1-continued

Characterisation of the Products

| | Elementary composition | | $^1$H—NMR-spectrum[1] | | | IR-spectrum[2] | | Mass spectrum[3] | | |
|---|---|---|---|---|---|---|---|---|---|---|
| | % C | % H | Chemical displacement | assignment | Multiplicity | Ester group | keto group C11 | OH | M+ | m/e[4] |
| | | | 6.31/6.34 7.18/7.31 | of 1-CH, 2-CH and 4-CH | | | | | | |
| 11-oxo-Δ1,4,17-BNC-methy ester | calc: 74.98 obs: 75.1/75.0 | 7.66 7.84/7.86 | | | | 1736 | 1707 | | 368 | |

[1]80 MHz solution in CDCl$_3$; chemical displacement expressed in ppm on the δ - scale, based on tetramethyl silane as the internal standard
[2]taken up in KBr; expressed as wave number (cm$^{-1}$)
[3]direct evaporation
[4]prominent peaks

EXAMPLE 3

Pregna-1,4,9(11)-triene-3-one-20-carbonyl chloride 0.3 ml of dry pyridine and 0.6 ml of thionyl chloride freshly distilled over aqualene are added at 0° C. to 718 mg of 11-β-hydroxy-pregna-1,4-diene-3-one-20-carboxylic acid in 20 ml of dry CH$_2$Cl$_2$. After 1 hour at °C., the reaction product is concentrated in vacuo to dryness. The still greasy residue is redissolved in a little methylene chloride and the resulting solution again concentrated to dryness.

An IR-spectrum of the residue in CHCl$_3$ shows that conversion into the carboxylic acid chloride is complete (bands at 1777, 1665, 1638 (shoulder), 1628, 1609 cm$^{-1}$).

The crude pregna-1,4,9(11)-triene-3-one-20-carbonyl chloride thus obtained may be further reacted without purification. The yield is best determined after esterification of the acid chloride.

EXAMPLE 4

Determining the yield of pregna-1,4,9(11)-triene-3-one-20-carbonyl chloride obtained in accordance with Example 3 by conversion into the methyl ester (pregna-1,4,9(11)-triene-3-one-20-carbonyl acid methyl ester)

The crude acid chloride obtained in accorance with Example 3 from 718 mg of the acid is dissolved in 15 ml of dry methylene chloride, followed by the addition of 0.6 ml of pyridine and 2 ml of methanol. After 1 hour, the reaction mixture is diluted with 20 ml of CH$_2$Cl$_2$ and the organic phase is successively washed with water, dilute H$_2$SO$_4$ and again with water, subsequently dried and finally concentrated, leaving as residue 700 mg of the crude tri-unsaturated methyl ester.

The $^1$H-spectrum confirms the postulated structure. Quantitative thin-layer crhomatogrphy shows a yield of 86 percent based on the acid used.

$^1$H-NMR (80 MHz, CDCl$_3$ δ-values); 0.70 (18-CH$_3$,s), 1.17 (21-CH$_3$, dJ=6.9 Hz), 1.40 (19-CH$_3$,s), 3.64 (—OCH$_3$,3), 5.48 (11-CH), ABC-system of 1-CH, 2-CH, 3-CH, 6.05, 6.18, 2.620, 6.31, 6.77, 7.23.

EXAMPLE 5

Pregna-1,4,9(11)-triene-3-one-20-carboxyamide

Pregna-1,4,9(11)-triene-3-one-carbonyl chloride obtained in accordance with Example 3 from 718 mg of 11-β-hydroxy-pregna-1,4-diene-3-one-20-carboxylic acid is dissolved in 20 ml of dry CH$_2$Cl$_2$. Gaseous NH$_3$ is slowly passed through the solution over a period of 2 hours at 0° C., after which the solution is poured into the same quantity of ice water, followed by careful acidification with dilute hydrochloric acid.

After phase separation, the aqueous phase is washed twice with methylene chloride and the combined CH$_2$Cl$_2$-phases are dried over Na$_2$SO$_4$. Removal of the drying agent and concentration of the solvent leaves 650 mg of a solid from which 500 mg of the required amide are obtained by chromatography over silica gel (eluent: CH$_2$Cl$_2$ (85), ethyl acetate (10) and ethanol (5)).

$^1$H-NMR (80 MHz, CDCl$_3$, of δ-values): 0.71 (18-CH$_3$, s), 1.20 (21-CH$_3$,dJ=6.4 Hz); 1.40 (19-CH$_3$), 5.48 (11-CH), ABC-system of 1-CH, 2-CH, 3-CH: 6.05, 6.18, 6.20, 6.31, 6.33, 7.12, 7.25.

EXAMPLE 6

Curtius degradation of a mixture of Δ$^{1,4,17(20)}$-BNC (55%) and Δ$^{1,4}$-BNC (45%)

0.4 ml of thionyl chloride freshly distilled over squalene are added at 0° C. to 1.7 g of the above-mentioned acid mixture in 10 ml of dry CH$_2$Cl$_2$, followed by stirring for 20 minutes at the temperature of 0° C. After concentration in vacuo at 0° C. to dryness, the residue is taken up again in CH$_2$Cl$_2$ and reconcentrated to dryness.

The mixture of acid chlorides is dissolved in 10 to 12 ml of dry CH$_2$Cl$_2$. 0.39 g of NaN$_3$ in approximately 1.5 ml of water and 10 mg of tetrabutyl ammonium chloride as phase transfer catalyst are added to the resulting solution at 0° C. After stirring for 20 minutes at 0° C., 2 ml of ice water are added, the phases are separated and washed with a little ice water.

The solution of the azides is added dropwise to approximately 20 ml of 70% acetic acid. The mixture is carefully heated to 60°–70° C., CH$_2$Cl$_2$ distilling off, and then kept for 30 minutes at that temperature. 20 ml of water are then added, followed by concentration in vacuo to dryness.

The residue is taken up in 20 ml of methylene chloride, 20 ml of 10% sodium hydroxide are added to the resulting solution and the product left standing overnight. After phase separation, the organic phase is washed until neutral, dried and concentrated, leaving 1.4 g of a crystalline residue which consists essentially of pregna-1,4-diene-3,20-dione and 20-amino-pregna-1,4-diene-3-one.

Pregna-1,4-diene-3,20-dione may be enriched in the ether phase by digesting this residue with ether. Filtration through a short column of silica gel (eluent: ethyl acetate/methylene chloride 80/20) gives 0.63 g (73%, based on Δ$^{1,4,17(20)}$-BNC) of amine-free, substantially pure pregna-1,4-diene-3,20-dione.

The total yield of 20-amino-pregna-1,4-diene-3-one, based on $\Delta^{1,4}$-BNC, amounted to 80% (as determined by quantitative TLC from the crude product after conversion into the acetamide).

EXAMPLE 7

Carboxy-inversion degradation of a mixture of $\Delta^{1,4,17(20)}$-BNC (55%) and $\Delta^{1,4}$-BNC (45%)

1.7 g of the total carboxylic acid mixture are converted as in Example 1 into the mixture of carboxylic acid chlorides. The solution of the acid chlorides in 10 ml of absolute methylene chloride is cooled to $-30°$ C., 1.0 g of dry m-chloro-perbenzoic acid (90%, remainder m-chlorobenzoic acid) in 10 ml of absolute $CH_2Cl_2$ and, finally, 0.48 g of dry pyridine in a little absolute $CH_2Cl_2$ are added dropwise thereto and the mixture is left overnight to return to room temperature.

Most of the solvent is removed in vacuo, 12.5 ml of 2 n methanolic potassium hydroxide are added at $0°$ C. to the residue, followed by stirring for several hours at room temperature. Most of the methanol is then distilled off in vacuo, the residue is taken up in methylene chloride and the methylene chloride phase is washed successively with water, dilute sulfuric acid and again with water, dried and the solvent is distilled off, leaving 1.4 g of a substantially crystalline residue which is chromatographed on a column of silica gel. 0.13 g of pregna-1,4,20-triene-3-one (from $\Delta^{1,4}$-BNC), 0.53 g of pregna-1,4-diene-3,20-dione (from $\Delta^{1,4,17(20)}$-BNC) and 0.34 g of 20 hydroxy-pregna-1,4-diene-3-one are successively eluted with methylene chloride/ethyl acetate (3 to 30% of ethyl acetate).

The preceeding specific embodiments are illustrative of the practice of the invention without being limitative in any respect. It is to be understood that other embodiments known to those skilled in the art or disclosed herein may be employed without departing from the spirit of the invention or the scope of the appended claims.

We claim:

1. A process of producing C20-carbonyl steroids from steroid C22-carboxylic acids by side chain degradation consisting essentially of:
   (1) reacting $\Delta^4(5)$-BNC-compounds with an additional ene-bond in the 17(20)-position having the formulae:

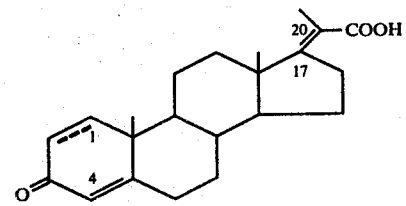
(1)

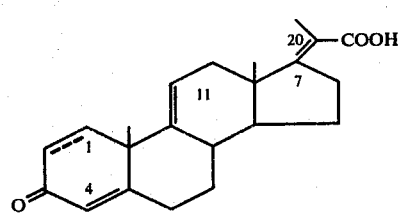
and (2)

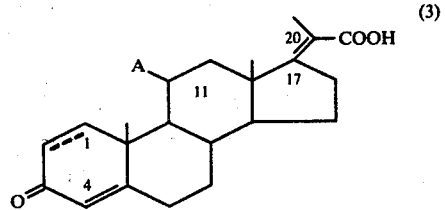
(3)

wherein A represents an $\alpha$-hydroxyl, a $\beta$-hydroxyl or, together with the carbon atom substituted by A, a carbonyl, with a carboxylic acid halogenating agent under conditions whereby unwanted ring halogenation products are avoided, to form the corresponding 22-carboxylic acid halide, (2) reacting the $\Delta^{17(20)}$-steroid-22-carboxylic acid halide with a metal azide in an aqueous/organic two-phase reaction in the presence of quaternary ammonium salts as a phase transfer catalyst at a temperature of below about 25° C., (3) hydrolyzing the azide formed by heating in the presence of an aqueous acid with elimination of nitrogen, and (4) recovering the corresponding C20-carbonyl steroid.

2. A process of producing C20-carbonyl steroids from steroid C22-carboxylic acids by side chain degradation consisting essentially of:
   (1) reacting $\Delta^{4(5)}$-BNC-compounds with an additional end-bond in the 17(20)-position having the formulae:

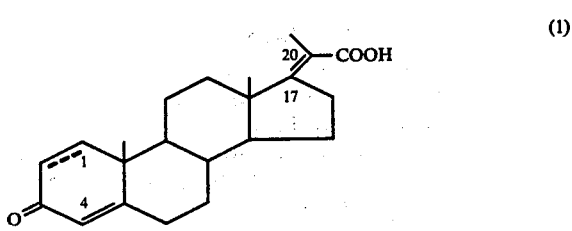
(1)

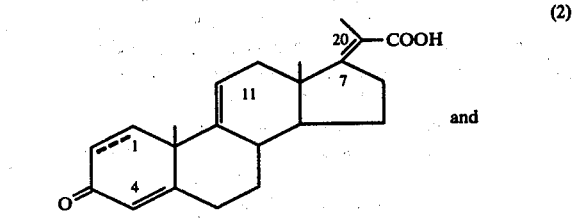
and (2)

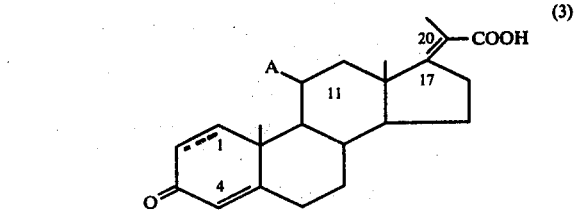
(3)

wherein A represents an $\alpha$-hydroxyl, a $\beta$-hydroxyl or, together with the carbon atom substituted by A, a carbonyl, with a carboxylic acid halogenating agent under conditions whereby unwanted ring halogenation products are avoided, to form the corresponding 22-carboxylic acid halide, (2) reacting the $\Delta^{17(20)}$-steroid-22-carboxylic acid halide with an aromatic percarboxylic acid at a temperature of from $-50°$ C. to about room temperature, (3) hydrolyzing the reaction product under basic/alcoholic conditions, and (4) recovering the corresponding C20-carbonyl steroid.

3. A process as claimed in claim 2, in which m-chloroperbenzoic acid is used as peracid.

4. A process as claimed in claim 2 in which the reaction is carried out in an inert solvent.

5. A process as claimed in claim 2 in which the reaction is effected in the presence of a basic compound.

6. A process as claimed in claim 5 in which the basic compound is a tertiary amine.

7. $\Delta^{4,17(20)}$-and $\Delta^{1,4,17(20)}$-BNC-compounds corresponding to formula I:

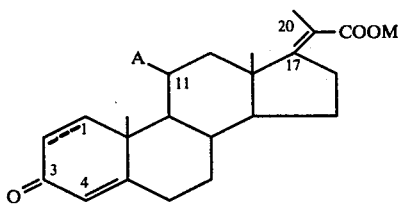

(I)

in which A represents a member selected from the group consisting of α-hydroxy, β-hydroxyl, and, together with the C-atom substituted by A, carbonyl and M represents a member selected from the group consisting of hydrogen, a salt-forming group and a hydrocarbon radical containing no more than 20 C-atoms.

8. 11-β-hydroxy-$\Delta^{1,4,17(20)}$-BNC.

9. 11-oxo-$\Delta^{1,4,17(20)}$-BNC.

10. A process for the production of new $\Delta^{4,17(20)}$-and or $\Delta^{4,17(20)}$-BNC-compounds corresponding to formula I:

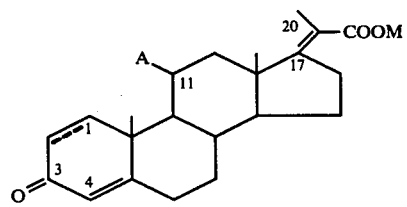

(I)

in which A is a member selected from the group consisting of hydroxyl, and, together with the C-atom substituted by A, carbonyl, and M represents a member selected from the group consisting of hydrogen, lower alkyl and a salt-forming group, in which structurally analogous BNC-compounds but without any oxygen in the 11-position are hydroxylated in the 11-position under aerobic conditions in an aqueous nutrient medium using microorganisms capable of 11-hydroxylation and the end products corresponding to formula I are recovered.

11. A process as claimed in claim 10 wherein 11-hydroxylated BNC-compounds corresponding to general formula I are oxidized to the 11-oxo-compounds.

12. A process as claimed in claim 10 or 11, characterized in that the free BNC-acids (M=H) or their salts soluble in the aqueous nutrient medium are subjected to the 11-hydroxylation.

13. A process as claimed in claim 12 in which the 20-carboxyl group is subsequently transformed into the ester group.

14. $\Delta^{4,9(11)}$-pregna-3-one-20-carboxylic acid compounds and related compounds containing at least one other double bond in the 1(2)- and/or 17(20)-position corresponding to formula I:

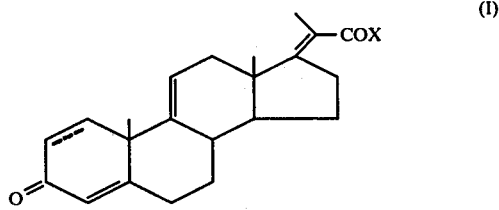

(I)

in which X is selected from the group consisting of OH, OR, halogen and NH$_2$, R represents a monovalent hydrocarbon having from 1 to 20 carbon atoms, with the priviso that when the compound is of the $\Delta^{1,4,9(11)}$-series, X is selected from the group consisting of halogen and NH$_2$.

15. Compounds as claimed in claim 14 in which X is selected from the group consisting of chlorine and bromine.

16. A process for the production of the $\Delta^{4,9(11)}$-pregna-3-one-20-carboxylic acid compounds of claim 15 which consists essentially of dehydrating structurally similar starting materials saturated in the 9(11)-position and hydroxylated in the 9- or 11-position to form the 9(11)-ene-bond and converting the product obtained to form the end products of formula I.

17. A process as claimed in claim 16 in which the 20-carboxylic acids or their esters are used as starting materials.

18. A process as claimed in claim 16 in which 9α- or 11β-hydroxylated starting compounds are used as starting materials.

19. A process as claimed in claim 16 to produce compounds corresponding to formula I, in which X is halogen wherein the corresponding steroid-20-carboxylic acid is reacted with from 1 to 3 molar excess of a halogenating agent at temperatures not exceeding 15° C.

20. A process as claimed in claim 19 in which the reaction of the steroid-20-carboxylic acid with the halogenating agent takes place at a temperature not exceeding 5° C.

21. A process as claimed in claim 19 or 20 in which a thionyl halide is used as the halogenating agent.

22. A process as claimed in claim 21 in which the thionyl halide is thionyl chloride.

23. A process as claimed in claim 16 or 17 or 18 in which to produce compounds corresponding to formula I in which X is NH$_2$ wherein the corresponding steroid-20-carboxylic acid is reacted with from 1 to 3 molar excess of a halogenating agent at temperatures not exceeding 15° C., the steroid-20-carboxylic acid halide formed is reacted with ammonia and/or an ammonia-yielding compound under the reaction conditions, and the desired steroid-20-carboxylic acid amide is recovered.

24. A process as claimed in claim 16 or 17 or 18 or 20 or 21 in which the 9(11) dehydration step and formation of the steroid-20-carboxylic acid halide are carried out in a single stage by using the halogenating agent in an excess over and above the quantity required for forming the carboxylic acid halide.

25. A process as claimed in claim 23 in which an approximately 1 to 1.5 molar excess of halogenating agent is used.

26. A process as claimed in claim 24 in which an approximately 1 to 1.5 molar excess of halogenating agent is used.

* * * * *